United States Patent [19]
Weuffen et al.

[11] Patent Number: 5,629,002
[45] Date of Patent: May 13, 1997

[54] COSMETIC OR PHARMACEUTIC PREPARATIONS FOR IMPROVING HAIR QUAILITY AND STIMULATING GROWTH OF THE HAIR

[76] Inventors: Wolfgang Weuffen, Ringstrasse 39, D-17498 Guest; Axel Kramer, Georg-Engel-Strasse 20, D-17489 Greifswald; Christel Tirsch, Rudolf-Weiss-Strasse 36, D-99947 Bad Langensalza; Hans Meffert, Oranienburgerstrasse 89, D-10178 Berlin; Stefan Koch, Schulstrasse 19, D-15526 Bad Saarow; Dagmar Sima, Meyerbeerstr. 50, D-13088 Berlin, all of Germany

[21] Appl. No.: 94,043

[22] PCT Filed: Jan. 11, 1992

[86] PCT No.: PCT/EP92/00048

§ 371 Date: Jul. 14, 1993

§ 102(e) Date: Oct. 26, 1993

[87] PCT Pub. No.: WO92/12699

PCT Pub. Date: Aug. 6, 1992

[30] Foreign Application Priority Data

Jan. 15, 1991 [DE] Germany ................. 41 00 975.4

[51] Int. Cl.$^6$ .................................................. A61K 7/06
[52] U.S. Cl. .................. 424/401; 424/70.1; 424/70.4; 424/70.5
[58] Field of Search ................ 424/70.4, 70.5, 424/702; 514/929, 880

[56] References Cited

U.S. PATENT DOCUMENTS

| | | | |
|---|---|---|---|
| 2,389,755 | 11/1945 | Baker | 167/87.1 |
| 5,227,164 | 7/1993 | Lundmark | 424/401 |
| 5,244,664 | 9/1993 | Godtfredsen | 424/401 |
| 5,252,325 | 10/1993 | Bires et al. | 424/401 |

FOREIGN PATENT DOCUMENTS

| | | |
|---|---|---|
| 0059428 | 2/1982 | European Pat. Off. |
| 0123528 | 10/1984 | European Pat. Off. |
| 0279244 | 8/1988 | European Pat. Off. |
| 0336236 | 10/1989 | European Pat. Off. |
| 3039281 | 10/1981 | Germany. |
| 3338339 | 4/1984 | Germany. |
| 3504695 | 8/1986 | Germany. |
| 3740576 | 6/1988 | Germany. |
| 61-233608 | 10/1986 | Japan. |
| 770561 | 3/1957 | United Kingdom. |
| 2144991 | 3/1985 | United Kingdom. |
| 2198132 | 6/1988 | United Kingdom. |
| 9012560 | 11/1990 | WIPO. |

OTHER PUBLICATIONS

Schmidt, et al., "Hyperprolaktinamie und hypophysare Hypothyreose als kofaktoren bei Hirsutismus und androgenum Haarausfall der Frau", *Hautarzt*, vol. 42 (1991), pp. 168–172.

Bergner et al., "Die Androgenetische Alopezie der frau", *Hautarzt*, vol. 42 (1991), pp. 201–210.

Meffert, et al., "Fotochemotherapie der Psoriasis mit 8–Methoxypsoralen und UV–A II–Binddung des Fotosensibilisators an Protein", *Derm. Mschr.*, vol. 162 (1976), pp. 887–892.

H. Janistyn, *Handouch der Kosmetika und Riechstoffe*, A. hüthig–Verlag, Heidelberg, vol. 1 (1968) pp. 285–302, 423–425, vol. 3 (1973), pp. 894–895.

R.S. Cole, "Light–Induced Crosslinking of DNA in the Presence of a Furocoumarin (Psoralen)", *Biochim. Biophys. Acta* (AMST.) 217 (1970) pp. 30–39.

W. Umbach, *Kosmetik: Entwicklung, Herstellung und Anwendung kosmetischer Mittel*, Georg Thieme–Verlag Stuttgart, New York (1988), table of contents.

Grant & Hackh's Chemical Dictionary, 5th Ed. (1987), p. 560.

Weuffen, et al., "Analytik und Vorkommen von Thiocyanat im Badewasser und in der Raumluft von Badekabinen des Schwefelbades Bad Langensalza/Bad Tennstedt,"*Z. Physiother.* 43 (1991), pp. 63–74.

"Emulgierender Cetylstearylalkohol,"*Deutsches Arzeneibuch* (1986), p. 628.

"Eiweiss–Hydrolsate," *Römpp Chemie Lexikon* (1990), pp. 1100–1101.

*Primary Examiner*—Thurman K. Page
*Assistant Examiner*—Sharon N. Howard
*Attorney, Agent, or Firm*—Fitzpatrick, Cella, Harper & Scinto

[57] ABSTRACT

The invention relates to cosmetic or pharmaceutical preparations for improving the quality of the hair and stimulating the growth of the hair, which preparations are based on A) alkali metal, alkaline earth metal and/or ammonium salts of thiocyanic acid in combination with B) at least one component, selected from estrogens, sulfur, sulfide ions, vasodilators, skin-active vitamins, inorganic selenium compounds, amino acids, protein hydrolyzates and carboxylic acids physiologically occurring in the skin or mixtures thereof. The preparations may optionally be in admixture with per se known auxiliary and carrier materials for hair cleaning and hair care agents. A synergistic improvement in the quality of hair and stimulation of hair growth is observed by combining the alkali metal, alkaline earth metal and/or ammonium salts of thiocyanic acid, with at least one of the component B) materials.

30 Claims, No Drawings

COSMETIC OR PHARMACEUTIC PREPARATIONS FOR IMPROVING HAIR QUAILITY AND STIMULATING GROWTH OF THE HAIR

The invention relates to cosmetic or pharmaceutic preparations for improving the quality of the hair and stimulating the growth of the hair, which preparations are based on alkali metal, alkaline earth metal and/or ammonium salts of thiocyanic acid, and to the use thereof.

From EP-0 336 236 A2 there has been known the application to man of physiologic salts of thiocyanic acid as a cosmetic agent for hair care, for maintaining and stimulating the growth of the hair and for increasing the resistance of the hair to harmful or noxious influences. According thereto, the salts of thiocyanic acid are also applicable to useful animals for increasing the yield and improving the quality (shine, coat structure, hair strength and elasticity, denseness and uniformity of the coat of hair, softness and tenacity during the processing operations) in the wool, fur, leather and/or feather production. The application route to man is mainly topical (in cosmetic or pharmaceutic preparations, e.g. as an additive to the bath water, hair tonic, shampoo and hair packs), while the application route to the useful animal is mostly oral, by admixing thiocyanate preparations to the fodder or by employing thiocyanate-enriched fodder.

It has further been known that placenta and its ingredients, e.g. estrogens and other hormones as well as allantoin, sulfur, disulfides, selenium, salts of heavy metals, antioxidants, vasodilators, vitamins, especially vitamin A, vitamins of the B group, in particular thiamine, vitamins of the D group, in particular vitamin $D_3$, pantothenic acid and tocopherol, amino acids, peptides, proteins or protein hydrolyzates, carboxylic acids, microbial, vegetable and animal extracts or extracts from human tissue, e.g. placenta, as well as natural and/or artificially generated UV radiation, also in combination with photosensitizers, can display a more or less stimulating influence on the growth of the hair. However, the effects achieved thereby, as a rule, are not significant and not reproducible in practice. In addition, a number of said active ingredients involves the danger of producing acute and chronic side-effects which would exclude any long-term application.

In the DE-PS 30 39 281 it is determined that the obviously noxious influence of $SCN^-$ caused by the use of raw materials of vegetable origin can be compensated only by using suitable compensating agents such as, e.g., copper (II) ions. Moreover, from said printed publication it is derivable that the amounts to be employed of $SCN^-$ are to be minimized to the lowest possible extent because of the obviously toxic effect. A restriction of the contents of $Cu^{2+}$ to from 1.5 to 6 mg/l and of $SCN^-$ to from 1 to 5 mg/l was provided for toxicologic reasons. In the proposed mixture, the $SCN^-$ content decreases in response to external influencing factors onto the redox potential (e.g. atmospheric oxygen, dust) irregularly, but altogether continuously. Under this aspect, the claimed contents of $Cu^{2+}$ and $SCN^-$ are not long term-stable biologically active and desirable additives. Nevertheless, at the same time there is only available a lower amount of $SCN^-$ due to the fast loss of free thiocyanate ions.

In EP-A-0 059 428 B1 EP-A0-059 428B1(AT-E-13-484) there has been described a hair treatment agent, in accordance with which cosmetic hair treatment agents comprising a protein hydrolyzate and alkali thiocyanates have been known, which agent imparts smoothness and softness to the hair and is reported to support an effective shaping without any undesirable tackiness. Any influence onto the growth of the hair (maintenance and stimulation) and the hair quality, such as increasing the resistance to harmful influences, has not been disclosed.

From DE 33 38 339 A1 there have been known active substances exhibiting a progesterone-like activity to reduce the dihydrotestosterone plasma level as agents for combatting alopecia of males.

It has been known that disorders of hormonal incretion may impair the healthy growth of hair. "This recognition led to employing hormones and steroids as active substances; however, the results are not unanimously assessed" (H. Janistyn, Handbuch der Kosmetika und Riechstoffe, 3rd volume, 1973, A. Hüthig-Verlag, Heidelberg, pp. 285 to 302 and 423 to 425). Schmidt et al. {Hautarzt (1991), 42, pages 168 to 172}, in subsequent investigations of the hormone levels of females upon an androgenic alopecia, could not determine any change in the estrogen level, while they observed an increase in cortisol, TSH and androstendione, whereby they substantiate hypothyreosis amd transient hyperprolactinemia as starting points for a causal therapy of androgenic alopecia.

Also T. Bergner and O. Braun-Falco {Hautarzt (1991), 42, pages 201 et seq.} subsequently draw attention to a multitude of contradictory hormone findings upon an androgenetic alopecia of females (AAF) and, thus, raise doubts of the therapeutic utility of an external application of estrogen-containing preparations.

From DE 35 04 695 A1 there has been known the action of vitamin E, blood circulation-promoting agents and skin-stimulating agents, and especially the action of vitamin E, onto the growth of the hair, which action is improved upon the addition of blood circulation-promoting, vasodilative and skin-stimulating agents.

Although it has been known, for example from H. Janistyn, Handbuch der Kosmetika und Riechstoffe, volume 1, 1968, A. Hüthig-Verlag, Heidelberg, pp. 894 to 895), that sulfur exhibits strong keratoplastic, regenerating and keratolytic effects which, in admixture with alkalis, may be so strong that even strong keratin formations (hair etc.) may be accomplished, nevertheless any direct statement relating to a stimulation of hair growth by sulfur has not been made. It has rather been observed in page 295 that "so far there is no hair tonic which is capable to regenerate the coat of hair of an obliterated scalp".

In DE 37 40 576 A1 there have been described certain 1-piperazinylpyrimidines (Minoxidil and derivatives thereof) for stimulating growth of the hair. Therein only retinoids have been mentioned as combination partners in addition to conventional carriers and auxiliary materials.

The stimulation of the growth of the hair—to the effect meaning an improvement in hair quality and hair formation upon loss of hair (alopecia in its various manifestations) upon the application of hair care agents or hair growth-stimulating agents—constitutes a cosmetic and/or pharmaceutic object which has only been incompletely attained in the state of the art (W. Umbach: Kosmetik. Entwicklung, Herstellung und Anwendung kosmetischer Mittel, Thieme-Verlag Stuttgart, New York 1988).

It is the object of the present invention to provide novel combinations of active substances, said combinations having been based on alkali metal, alkaline earth metal and/or ammonium salts of thiocyanic acid, as constituents in cosmetic or pharmaceutical compositions, including hair care preparations, to attain the following objectives:

Improvement of the hair quality and of the properties of the hair—to ensure the formation of healthy hair and the improvement in quality associated therewith of the hair as regards shine, elasticity, denseness, uniformity, softness, strength and shapability;

Prevention of hair damages and subsequent loss of hair: This above all means the reduction of hair-damaging influences, e.g. those caused by a permanent, by hair dying or tinting or by ambient influences;

Stimulation of new hair formation in healthy humans or in the case of diseases, inclusive toxic stresses: If the growth of hair is deteriorated by toxic influences, for example by cytostatic therapy, harmful commercial or environmental substances, a growth-maintaining and -stimulating effect is desired.

The above-mentioned demands can be met by pharmaceutic or cosmetic preparations for improving, which preparations are based on alkali metal, alkaline earth metal and/or ammonium salts of thiocyanic acid and are characterized in that they contain, as a further constituent, at least one component or mixtures of components selected from estrogens, sulfur, sulfide ions, vasodilators, skin-active vitamins, inorganic selenium compounds, amino acids and carboxylic acids physiologically occuring in the skin, optionally in admixture with per se known auxiliary and carrier materials for hair cleaning and hair care agents. In the same manner the above-mentioned objects can be attained by pharmaceutic preparations which contain, as a further component in addition to the thiocyanic acid, protein hydrolyzates. Another subject matter of the present invention is the use of said salts of thiocyanic acids and protein hydrolyzates for improving the quality of the hair and stimulating the growth of the hair.

Surprisingly it has been found that cosmetic or pharmaceutic preparations based on alkali metal, alkaline earth metal and/or ammonium salts of thiocyanic acid and containing further components which in part are intended to display a stimulating influence onto hair properties and hair growth in the combinations described according to the invention cause a significant improvement in hair quality and/or stimulation of the growth of the hair, which effects do by far exceed the additive effects that were to be expected. By means of the combinations according to the invention of active substances, there are throughout accomplished synergistic effects. The term "synergistic effects" as used within the present invention is intended to also pertain to those effects with respect to which the further constituent— employed in addition to the active materials containing the alkali metal, alkaline earth metal and/or ammonium salts of thiocyanic acid—alone by itself does not cause any sufficient improvement in hair quality and/or stimulation of the growth of the hair.

Although basically any physiologically compatible thiocyanate which will form thiocyanic acid upon hydrolysis may be employed within the scope of the present invention, preferred cosmetic or pharmaceutic preparations contain alkali metal salts of thiocyanic acid, which salts preferably are selected from those of sodium and potassium.

Preferred concentrations of the alkali metal and/or alkaline earth metal salts of thiocyanic acid have already been known from EP-0 336 236 A2, so that the preferred pharmaceutic or cosmetic preparations may contain thiocyanate ions, in particular, in a concentration of from 0.01 to 1% by weight, based on the weight of the preparation.

It has been known from the dermatologists' practical experiences that preparations containing estrogens at best display a low hair growth-stimulating effect which is difficult to reproduce and is limited to a small group of patients. In view of more recent insight into fundamentals and a lack in convincing studies the therapeutic effect of an external administration of estrogen is subject to increasing doubts (Bergner and Braun-Falco, loc. cit.). However, with the present invention it was found that preparations which contain, as estrogen, estradiol, especially in the form of estradiol benzoate, in a concentration of from 0.002 to 6 mg/l, relative to the preparation, in addition to the alkali metal, alkaline earth metal and/or ammonium salts of thiocyanic acid, in comparison to a treatment with the individual active ingredients, exhibit a significantly strong effect against loss of hair caused by androgens. Evidence has been furnished of that estrogens may also reduce the growth activities of healthy hair, i.e. in the absence of androgenic disorders of the hair formation, while this effect is virtually completely reversed by $SCN^-$ ions; this offers the option of applying a combination of both active substances, whereby unforeseeable influences by the estrogens can be compensated and an absolutely new coergism occurs.

Upon the addition of thiocyanate ions to the estrogen-containing aqueous-alcoholic solution, the effectivity thereof was potentiated, and thereby the combination preparation proved to be effective to patients suffering from androgenic disorders of hair formation, thus exhibiting a thiocyanate activity which was not provided by thiocyanate as an individual active substance in EP-0 336 236 A2.

By employing the combination comprising estrogen which affects hormonal disorders and thiocyanate as an active substance affecting cell metabolism as well as the estrogen receptor, the efficiency of the hair growth stimulation by thiocyanate ions can be potentiated. It is to be assumed that an increased receptor potential, inter alia, results from the thiocyanate-mediated cell activity, such as to provide a higher binding capacity for binding estradiol to this receptor.

The synergism-dependent effects provided by the combination allows the hormone dose to be reduced to from one fifth to one third of the amount usually employed of estrogens, in particular estradiol benzoate, for influencing hair growth, i.e. to 2 mg, whereby the risk of known systemic side effects, e.g. gynecomastia and testicular atrophy, is considerably reduced and at the same time the risk of undesirable side effects onto the growth of the hair is lowered.

By way of undergoing a course treatment of sulfur baths in combination with thiocyanate-containing preparations, an effect of the thiocyanate administration for hair care and for the stimulation of the growth of the hair could be enhanced in a surprising manner.

Thus, patients suffering from various forms of alopecia over several weeks received a course treatment in a sulfur spa (Bad Langensalza, Thuringia), where divalent sulfur is biochemically generated by the activity of microorganisms in a sulfate-containing ground water.

Whereas previously the patients who suffered from therapy-resistant alopecia forms had undergone unsuccessful treatments for years, immediately after the treatment in the spa follicles which first had been atrophic became accentuated, and the single hair became visible in the ostium. At the same time the activity of the beginning hair growth was non-uniformly distributed over the area. After several months, especially in the past period of subsequent observation over 2 years, the effect was stable. With part of the patients an improvement of seborrhea could be observed, and one patient showed an improved sebostasis. The acid-protective layer on the skin was not adversely affected; no other side-effects were observed either. More specifically, the thyroid function remained unaffected, as has been expected.

Accordingly, a further embodiment of the present invention consists of a cosmetic or pharmaceutic preparation based on alkali metal, alkaline earth metal and/or ammonium salts of thiocyanic acid, which preparation contains sulfur in the form of colloidal sulfur, especially in a concentration of from 0.01 to 20 mg/l, based on the preparation. For a potentiation of the improvement of the hair quality and/or stimulation of the hair growth by alkali metal, alkaline earth metal and/or ammonium salts of thiocyanic acid, the action of divalent sulfur and of further natural ingredients contained in the warm health spas may be contemplated. This is applicable, inter alia, also to increasing the blood circulation in combination with enhancing the cell metabolism and to providing divalent sulfur. It is further noteworthy that in the natural remedies an amount—although extremely low and insignificant to said effect—of thiocyanate is contained (about from 7 to 15 μg/l).

In a further embodiment of the present invention the importance of the blood circulation in the scalp for the healthy condition of the hair was studied, and the efficiency of the thiocyanate application with locally active vasodilators as per se known in the art and used in the medicament sector. By combining alkali metal, alkaline earth metal and/or ammonium salts of thiocyanic acid with vasodilators, a potentiation of the effect could be observed in comparison to the efficiency of the individual components, detectable by a change in the stages of hair growth in favor of the anagenic phase. Accordingly, one preferred embodiment of the cosmetic or pharmaceutic preparations, based on alkali metal, alkaline earth metal and/or ammonium salts of thiocyanic acid according to the invention for improving the hair quality and/or stimulating the growth of the hair, consists of that it contains propyl nicotinate as a vasodilator, especially in a concentration of from 1 to 50 mg/l, relative to the preparation.

It could be verified that upon the administration of propyl nicotinate alone any statistically significant hair growth stimulation was not observable. However, a considerable stimulation of the growth of hair could be observed upon the use of a combination of sodium thiocyanate with propyl nicotinate, which effect was clearly superior to a corresponding hair growth stimulation induced by thiosulfate alone.

The improved blood circulation—which in the moment of application may be classified as hyperemia—appears to ensure an accelerated and more uniform infiltration of the thiocyanate ions. This results in a potentiation of the effect afforded onto hair growth by the two materials employed. This beneficial effect, thus, is of importance not only for the treatment of alopecia forms, but according to the recognitions of the present invention it also results in a simultaneous improvement in the hair formation of healthy persons.

Upon the application of skin-active vitamins, for example of panthenol, a synergistic combination effect could be observed. The treatment was effected by applying an aqueous thiocyanate solution onto the skin and hair and causing it to be absorbed by massage. A panthenol spray was applied thereafter, also caused to be absorbed with massage, and a later on a hair wash was carried out. Hereby, the denseness of the hair and the hair properties could be distinctly improved over an individual application of the compounds. Apparently, the topical application of skin-active vitamins stimulates cell metabolism and thereby enhances the metabolic effect of the thiocyanate.

Accordingly, one preferred embodiment of the present invention consists of a preparation as defined above, said preparation containing Dexpanthenol as a skin-active vitamin, more specifically in a concentration of from 1 to 50 g/l, and especially of from 1 to 5 g/l, relative to the preparation.

In a preferred embodiment of the present invention the effect of a combination of thiocyanates with selenium compounds was studied. Here, a significant shift from the growth phase to the anagenic growth phase could be observed. Hence, a preferred embodiment of the present invention consists of preparations containing alkali metal selenocyanates, more specifically in a concentration of from 0.01 to 5 mg/l, relative to the preparation. A particularly preferred alkali metal selenocyanate within is the scope of the invention is potassium selenocyanate.

The activity of a combination of sodium thiocyanate with short-chain and higher molecular weight peptides and/or proteins in the form of Aminofusin-Hepar infusion solutions was studied with test persons suffering from alopecia. The preparations were administered as hair packs, followed by a conventional hair wash using a shampoo.

Due to the interaction between the above-identified combined substances there is a distinct enhancement of the thiocyanate effect with respect to hair growth. This, more particularly, concerns the shine and shapability of the hair. Further on there may be an improved bioavailability of thiocyanate as a result of the added short-chain and higher molecular weight peptides or proteins, respectively, due to a higher dispersion caused by hydrophobic interactions and coordinative binding forces. Accordingly, one further preferred embodiment of the present invention consists of preparations containing amino acids or mixtures of amino acids and/or protein hydrolyzates in a total concentration of from 1 to 150 g/l, preferably from 10 to 80 g/l, relative to the preparation.

Also studied was the effect provided by a combination of thiocyanates and short-chain carboxylic acids which physiologically occur in the skin. As a representative of this group there was investigated lactic acid, which when applied alone did not exhibit any significant influence onto the growth of the hair. However, evidence could be furnished of the synergistic effect of thiocyanate and carboxylic acids which physiologically occur in the skin by way of a shift of the growth phase towards the anagenic phase. Accordingly, one further preferred embodiment of the present invention consists of preparations containing lactic acid as a carboxylic acid which physiologically occurs in the skin, especially in a concentration of from 1 to 100 g/l, relative to the preparation.

The pharmaceutic or cosmetic preparations for improving the quality of the hair and stimulating the growth of the hair, which preparations are based on alkali metal, alkaline earth metal and/or ammonium salts of thiocyanic acid, optionally contain auxiliary and carrier materials per se known in the art for hair cleaning agents and hair care agents. Such auxiliary and carrier materials for hair cleaning agents and hair care agents are, for example, ethanols, glycerols, alkali metal alkanesulfates, alkali metal alkanesulfonates, polyethyleneglycols, wool wax alcohols, triglycerides, Sapamine, *Alcoholes emulsivicantes* (F. Winter, Handbuch der gesamten Parfümerie und Kosmetik, Springer Verlag Wien 1952, 6th Edition). Especially preferred for the topical application are solutions, emulsions, dispersions, gels and/or ointments.

Within the scope of the present invention it is not required that the alkali metal, alkaline earth metal and/or ammonium salts of thiocyanic acid and the further components resulting in a synergistic improvement of the quality of the hair and stimulation of the growth of the hair are present in one and the same solution, emulsion, dispersion, gel or ointment. Pharmaceutic or cosmetic preparations according to the invention also include those preparations wherein said components may be present separately from each other, leaving the option of a simultaneous or deferred application.

The most advantageous timing of the application of the individual components may be readily determined by means of simple tests and observation of the effects. Thus, one further embodiment of the present invention consists of preparations which are characterized in that the alkali metal, alkaline earth metal and/or ammonium salts of thiocyanic acid and the further components are present separately from each other, optionally each in combination with per se known auxiliary and carrier materials.

Although the use of the preparations for improving the quality of the hair and stimulating the growth of the hair basically is not subject to any restriction, one embodiment of the present invention consists of use of the preparation for a topical application, optionally in medical bath waters, shower lotions, hair tonics, hair shampoos, hair care agents and/or cosmetics. Thus, more specifically, the present invention relates to the use of the preparations for improving the quality of the hair and the properties of the hair, the prevention of damages to the hair and subsequent loss of the hair, and to stimulating the growth of the hair, especially upon alopecia, e.g. if the alopecia has toxic, metabolic or genetic causes. Accordingly, the pharmaceutic or cosmetic preparations may be applied in the form of solutions, emulsions, dispersions, gels and/or ointments.

The effect provided by a combination of thiocyanate ions and a physiologically actie ultraviolet radiation was studied in a further test series. Test persons suffering from an *Alopecia totalis* were subjected to a UV irradiation of the whole body in the form of the PUVA therapy (combination of 8-methoxy-psoralen with UV-A radiation), and sodium thiocyanate was applied as a hair pack. Upon the combined application of sodium thiocyanate and PUVA therapy, hair began to grow, and an increased growth of the hair, relative to the area and hair denseness, could be observed in comparison to the application of sodium thiocyanate alone.

It appears that in this combination an effect proven by Meffert et al. {H. Meffert, W. Dietzel, W. Günther and N. S önnichsen, Photochemotherapie der Psoriasis mit 8-Methoxypsoralen und UV-A II-Bindung des Photosensibilisators an Protein; Derm. Mschr. 162 (1976), pages 887–892} is relevant, according to which effect 8-methoxypsoralen binds also to structures other than nucleic acids {R. S. Cole, Light-Induced Crosslinking of DNA in the Presence of a Furocoumarin (Psoralen); Biochim. Biophys. Acta (AMST.) 217 (1970), pages 30–39}, especially to proteins, so that the action also proceeds via changes on cellular membranes.

In addition, investigations with guinea pigs were carried out in order to elucidate possible mechanisms of action. In guinea pigs, UV radiation induced a decrease in the thiocyanate content of the skin and counteracted a stress-related thiocyanate increase as determinable in the serum in a control group.

It is assumed that upon the formation of free radicals and via consecutive reactions the available thiocyanate, which is determinable not only in the skin, but also in the serum, undergoes a reaction. Upon the simultaneous local application of thiocyanate, the depots thereof are refilled again, which could be an essential reason for the synergistic effect of the combined application of UV-A irradiation and local application of thiocyanate.

EXAMPLES

Example 1

An alcoholic solution having the following composition was applied once a week to five male test persons suffering from androgenic alopecia after a hair-wash using a commercially available shampoo:

| Estradiol benzoate | 2 mg |
|---|---|
| Sodium thiocyanate | 27.4 mg |
| Ethanol, 70% | ad 1000 ml. |

The growth of the hair was evaluated in accordance with the following Table 1.

TABLE 1

Area-related

0 = no growth
2 = 10 to 40% growth in comparison to complete hair growth
4 = >40 to 60% growth in comparison to complete hair growth
6 = >60 to 80% growth in comparison to complete hair growth
8 = >80 to 100% growth in comparison to complete hair growth
Hair denseness-related 0.5 = very low hair denseness
1.0 = low hair denseness
1.5 = moderate hair denseness
2.0 = good hair denseness
Relative to properties of the hair such as elasticity, shapeability and shine 0.5 = very low
1.0 = low
1.5 = moderate
2.0 = good The maximum score attainable was 12 points.

Each scalp and hair were intensely wetted with the alcoholic solution and then massaged for about one minute. The test persons had used the alcoholic solution without the addition of thiocyanate, but only with the addition of 6 mg of estradiol benzoate, already for three to five years, during which the hair became increasingly sparse while no improvement of the hair was clinically manifest.

Upon the application of the combination of thiocyanate and estrogen a stimulation of the growth of the hair could be determined which, on the average, was in the magnitude of 1.8 steps, relative to the initial condition.

Comparative Example 1

Sodium thiocyanate alone at a dosage of 27.4 mg/l in 70% ethanol was applied once a week to five male test persons of the same treatment group in the same manner as in Example 1. There could be determined a stimulation of the growth of the hair by only 1.1 steps.

Comparative Example 2

A third group of test persons also comprising five persons was given the estrogen-containing alcoholic solution in the same manner as in Example 1; said solution contained 2 mg of estradiol benzoate in 1 liter of 70% ethanol. No stimulation of the growth of the hair could be determined.

Example 2

Patients suffering from androgenic alopecia received hair packs with the estrogen-containing ethanolic formulations of Example 1 for periods of 10 minutes. The alopecia forms of all of the patients were therapy-resistant. All other therapy forms were discontinued at least three months before the beginning of the clinical test. Four months after the end of the therapy the area-related growth of the hair was evaluated in the same manner as in Table 1. When thiocyanate was added to an estrogen-containing alcoholic solution, its effectivity was potentiated, as is evident from Table 2. Thereby the effectivity of thiocyanate, which was not observed in prior art with thiocyanate as the only active substance, against hair loss was accomplished for both groups of patients exhibiting androgenic disorders of hair formation by the above-identified combination.

Comparative Example 3

In the same manner as in Example 2, patients suffering from androgenic alopecia received hair packs with thiocyanate without estrogen also for a period of 10 minutes. The following Table 2 shows the stimulation of the growth of the hair of male patients suffering from androgenic alopecia by thiocyanate in combination with estradiol benzoate and by thiocyanate alone, both in an ethanolic solution.

TABLE 2

| | Area-related hair growth (cf. Table 1) | | | |
|---|---|---|---|---|
| | Example 2 Thiocyanate-estradiol-benzoate in ethanolic solution | | Comparative Example 3 Thiocyanate in ethanolic solution | |
| Patient | Initial result | Result after 4 months | Initial result | Result after 4 months |
| 1 | 2 | 6 | 2 | 6 |
| 2 | 2 | 6 | 0 | 2 |
| 3 | 0 | 4 | 2 | 4 |
| 4 | 2 | 8 | 2 | 2 |
| 5 | 0 | 2 | 2 | 2 |
| Sum | 6 | 26 | 8 | 16 |

Growth was not affected by an alcoholic solution which contained estrogen alone.

The effectivity of the hair growth-stimulation by thiocyanate was potentiated by the combination with the estrogen influencing hormonal control and the active substance thiocyanate influencing cell metabolism as well as estrogen receptors. It may be assumed that an elevated receptor potential, inter alia, results from the thiocyanate-mediated cellular activation and, hence, a higher binding capacity for estradiol to its receptor is available.

Due to the beneficial combination effect, it is possible to reduce the hormone dose to from one fifth to one third of the amount usually employed of estrogens for influencing hair growth, i.e. to 2 mg, the risk of known systemic side effects, e.g. gynecomastia and testicular atrophy, is reduced.

Example 3

Using albino guinea pigs, the effectivity of the combination of estrogens with thiocyanate was compared to the effectivity of the individual components. The following groups were formed:

K 1 Control groups=Application of drinking water

K 2=Application of 70% ethanol

T 1 Therapy groups=Application of sodium thiocyanate (300 mg of SCN⁻/l of drinking water)

T 2=Application of sodium thiocyanate (300 mg of SCN⁻/l of 70% ethanol)

T 3=Application of sodium thiocyanate (300 mg of SCN⁻/l of 70% ethanol) with the addition of 2 mg of estradiol benzoate T 4=Application of 2 mg of estradiol benzoate/l of 70% ethanol.

The animals were electrically shaved on a back area of about 3 cm×5 cm in size, then chemically depilated using barium sulfide, and the application was begun on the following day. The test solution was rubbed in by massaging on the shaved area of each animal within 30 seconds twice a day between 7 and 8:30 a.m. and between 7 and 9 p.m., whereby the adjacent coat was also wetted. Then the animals, having still a wet coat, were placed in their cages again. An application-free interval was maintained over the weekends. The animals were again shaved every 7 days, the last time two weeks before the termination of the test. The period of application comprised 30 days, while the total test took a period of 6 weeks.

On day 14 after the last depilation, the thickness of the hair, the denseness of the hair and the follicle cycle phases were determined in accordance with Orfanos (Orfanos, C. E.: Haar und Haarkrankheiten; Fischer-Verlag Stuttgart/New York, 1979). Prior to the investigation the hairs were embedded in Eukitt® (O. Kindler GmbH, Mikroskopische Gläser, Ziegelhofstr. 214, D-7800 Freiburg i.Br.).

Drinking water and ethanol (K 1 and K 2) did not exert any effect onto the growth of the hair. The effect provided by the aqueous thiocyanate solution (T 1) was enhanced by thiocyanate-containing ethanol (T 2) and became more distinct by the combination with estradiol benzoate and ethanol, the effect of the latter being significantly superior to the effects provided by the combinations of estradiol benzoate and of thiocyanate, respectively, with ethanol.

Example 4

Tests were carried out in the same manner as in Example 3, however with the proviso that only in group T 4 an amount of 6 mg of estradiol benzoate/l of 70% ethanol was employed, in the month of November, that is in a phase characterized by the change from the summer coat to the winter coat, which change superimposes the mosaic molt. The groups K 1, K 2 and T 1 through T 3 were identical to those in Example 3.

In the specified period of coat change, the growth of the hair in the tendency by estradiol benzoate is significantly reduced by ethanol (cf. Table 3). Apparently, estrogens are capable of reducing the activity of hair growth in phases of an enhanced hair growth. The unfavorable estrogen effect is virtually reversed by the combination with thiocyanate (cf. Table 3), which means that, surprisingly, there is a synergism. This provides the option of employing the combination of estrogens with thiocyanates, if the medical indication of an estrogen application is valid, whereby possible negative, uncontrollable influences of the estrogens onto the growth of the hair are compensated. To the effect the same, although not quite as distinct, is applicable to the use of alcohols, e.g. in hair tonics.

TABLE 3

| Influence of thiocyanate, ethanol and estradiol benzoate alone and in combination onto the growth of the hair | | | |
|---|---|---|---|
| Test group | Hair Cycle | | |
| | Anagen phase | Katagen phase | Telogen phase |
| K1 | 52.4 (100%) | 13.8 (100%) | 30.5 (100%) |
| K2 | 46.9 (89.5%) | 23.8 (172.8%) | 28.2 (92.4%) |
| T1 | 68.4 (130.6%) | 12.3 (89.5%) | 19.3 (63.2%) |

TABLE 3-continued

Influence of thiocyanate, ethanol and estradiol benzoate alone and in combination onto the growth of the hair

| Test group | Hair Cycle | | |
|---|---|---|---|
| | Anagen phase | Katagen phase | Telogen phase |
| T2 | 63.8 (121.7%) | 10.8 (78.3%) | 22.4 (73.4%) |
| T3 | 50.3 (96%) | 16 (116.3%) | 26 (85.2%) |
| T4 | 38.1 (72.8%) | 28 (203.6%) | 26.7 (87.5%) |

Example 5

Test persons suffering from different alopecia forms such as A. totalis, A. areata and A. diffusa received a course treatment in a sulfur spa for four weeks. The water was a natural healing water in Bad Langensalza, Thuringia, where divalent sulfur is biochemically generated by the activity of microorganisms in a sulfate-containing ground water. The concentration of titratable sulfur is 32 mg/l of healing water on the average all over the year.

Three groups of test persons were formed. Each test person in all of the three groups received a daily full bath (36° C.) for 20 minutes and hair packs two to three times a week. The general regimen of the applications of three groups is set forth in the following Table 4.

TABLE 4

| Test parameter | Remarks |
|---|---|
| 1. Therapy-free interval | At least 3 month before the beginning of the therapy |
| 2. Hair care | Only commercially available shampoo allowed as additional measure |
| 3. Amount | Thirty ml per treatment |
| 4. Application | Apply the preparation and massage it into the scalp by careful rubbing, then in the case of sufficient coat of hair cover it with a plastic hood for the period of action, in the case of poor coat of hair first apply dressing gauze for retaining the liquid and then put on the plastic hood |
| 5. Period of action | Remove pack after 20 minutes, comb the scalp; hairwash 2 hours later |
| 6. Cycle of application | Three treatments a week over four weeks, 12 treatments in total |

The test persons in the control group received a hair pack using the healing water, i.e. the sulfur-containing water. The second group of test persons received a hair pack with drinking water containing thiocyanate as an additive in an amount of 10 mg of $SCN^-$ per 30 ml of water. The third group of test persons was treated analogously, but using the same dose of thiocyanate in sulfur-containing water.

All test persons suffered from therapy-resistant forms of alopecia, i.e. other alopecia treatments over years had been unsuccessful.

All of the other therapy forms were discontinued at least three months before the beginning of the clinical test.

The following conditions, inter alia, were examined prior to the course treatment, immediately after the course treatment and up to two years after the course treatment:

Cinical evaluation of the growth of the hair in accordance with the evaluation scale of Table 1;

Trichogram according to Orfanos;

Determination of thyroid hormone;

Zinc and iron serum level (Note: Persons suffering from zinc or iron deficiencies were not included in the treatment groups);

Clinical evaluation of the Status seborrhoicus;

Further assessment of the skin functions such as determination of the resistance to alkali, nitrazine yellow test and determination of the roughness of the skin.

The results of the course treatment given to alopecia patients over four weeks with a combination of thiocyanate and a sulfur bath are summarized in the following Table 5. As will be apparent from the Table 5, the effect of the sulfur-containing water is distinctly enhanced by thiocyanate. Immediately after the treatment in the spa follicles which first had been atrophic became accentuated, and the single hair became visible in the ostium. At the same time the activity of the beginning hair growth was non-uniformly distributed over the area. After about three months, growth of the hair became clearly visible, the maximum—especially the area-related maximum—being observed between the 3rd and 6th months. In the past period of subsequent observation over 2 years, the effect was stable. Furtheron, the addition of thiocyanate to the sulfur-containing water caused an improvement of the seborrhea in 6 of 8 test persons and an improvement of the sebostasis in 1 of 11 test persons. The acid-protective layer on the skin was not adversely affected; no other side-effects were observed either. More specifically, the thyroid function remained unaffected, as has been expected.

TABLE 5

| Active Substance | Diagnosis | Smoking behavior | | | | Average initial condition | | Extent of hair growth after one year (area-related, cf. Table 1) | | | | | | | | | |
|---|---|---|---|---|---|---|---|---|---|---|---|---|---|---|---|---|---|
| | | Non-smoker | | Smoker | | | | Male patients | | | | | Female patients | | | | |
| | | o | o | o | o | o | o | 0 | 2 | 4 | 6 | 8 | 0 | 2 | 4 | 6 | 8 |
| Sulfur-containing water* | Alopecia (A.) areata | 0 | 3 | 2 | 3 | 2.0 | 6.3 | | | 1 | | 1 | | 2 | 2 | 1 | 1 |
| | A. diffusa | | 1 | | | | 4.0 | | | | | | | | | 1 | | |
| | A. totalis | 1 | 1 | 1 | 1 | | | 1 | 1 | | | | | 2 | | | | |
| | | 1 | 9 | 3 | 7 | 1.0 | 4.7 | | | 3.5 | | | | | 3.6 | | |
| Thiocyanate-containing water* | A. areata | 1 | 2 | 1 | 2 | 3.0 | 2.4 | | | | 2 | | | | 3 | | 1 |
| | A. diffusa | 1 | 2 | | | 2.0 | 2.0 | | 1 | | | | | | | 2 | | |
| | A. totalis | 2 | 1 | 1 | | | | | 2 | 1 | | | 1 | | | | | 1 |

TABLE 5-continued

| Active Substance | Diagnosis | Smoking behavior | | | | Average initial condition | | Extent of hair growth after one year (area-related, cf. Table 1) | | | | | | | | | |
|---|---|---|---|---|---|---|---|---|---|---|---|---|---|---|---|---|---|
| | | Non-smoker | | Smoker | | | | Male patients | | | | | Female patients | | | | |
| | | o | o | o | o | o | o | 0 | 2 | 4 | 6 | 8 | 0 | 2 | 4 | 6 | 8 |
| Combination of sulfur-containing water with thiocyanate | A. areata A. diffusa A. totalis | 4 1  4 5 | 5 2  1 3 | 2 2 2 2 | 3 2 2 4 | 1.3 2.0  0.9 | 3.7 4.0 3.0  3.1 | 1 | 1 | 5.0 1 1 6.0 | 2 2 | | 1 | 4.8 2 | 2 1 | 1 1 1 | | 5.4 |

*Comparative Example

Example 6

With view to the importance—which, dependent on the circumstances, may be substantial—of the blood circulation in the scalp for the health of the hair, the effectivity of the SCN⁻ application was examined using a commercially available locally active vasodilator (see also Example 7).

In the same manner as in Example 3 the combination of NaSCN (300 mg of SCN⁻ per 1 liter of 50% propan-2-ol) and propyl nicotinate (5% content of the active ingredient in a 70% ethanolic solution) was compared with the effectivity of each of the active ingredients when applied alone.

The combination resulted in a potentiation of the effect, in comparison to the effects provided by either of the single components, detectable by the change of the hair growth stages in favor of the anagenic phase.

Example 7

In the ambulatory dermatological practice, the effectivity of monotherapies applying each of the hyperemizing substance propyl nicotinate (5% in 70% ethanol), sodium thiocyanate (27.4 mg/l of 70% ethanol) and 70% ethanol alone was compared with that of the combination of both of the active substances at the same doses in 70% ethanol.

During the period of examination no statistically significant stimulation of the growth of the hair was determinable upon the application of propyl nicotinate in an ethanolic solution as well as upon the application of ethanol alone. A convincing stimulation of the growth of the hair was determinable upon the application of the combination of sodium thiocyanate and propyl nicotinate which was superior by 0.7 points, according to Table 1, to that of the use of thiocyanate alone.

Example 8

Over an application period of three months (application three times a week), the application was studied of a combination of a panthenol spray (Content per 100 g: 4.26 g of Dexpanthenol) and sodium thiocyanate (27.4 mg of SCN⁻ per 1 liter of drinking water) in comparison to the individual components; the test persons earlier had undergone unsuccessful dermatological treatments against an increasing loss of hair for years. The applications were given to 5 test persons in each group.

The therapy by combination treatment was carried out by first applying the aqueous thiocyanate solution to the scalp and massaging same for about 1 minute. Then the panthenol spray was applied, also followed by massaging, and 2 hours later a hairwash was carried out. The individual components were applied in a similar procedure, i.e. application of the test substance and 2 hours later doing a hairwash.

While no influence of panthenol spray alone was detectable, the effectivity of thiocyanate (improvement of the hair denseness and hair properties by 0.7 points according to Table 1) was clearly improved by the subsequent panthenol application (1.4 points according to Table 1).

Example 9

In accordance with Example 3, the effect achieved by a combination of potassium selenocyanate and thiocyanate was tested with guinea pigs. To this end, potassium selenocyanate (0.1 mg) and sodium thiocyanate (20 mg) were tested in 1 liter of drinking water. Furtheron, the same doses were applied of either of the components alone.

In comparison to the individual components, a significant shift towards the anagenic growth phase was accomplished, i.e. the effect caused by the individual components was potentiated.

Example 10

The effectivity of a combination of sodium thiocyanate with short-chain as well as higher molecular weight peptides and/or proteins in the form of human hair hydrolyzate (10% of protein digestion products in the final formulation) and with amino acids in the form of Aminofusin-Hepar® infusion solution was tested on 5 test persons suffering from alopecia; the composition of the Aminofusin-Hepar® infusion solution was as follows: Contents per 1 liter: Amino acids 50 g, corresponding to 7.59 g of N (isoleucine 7.6 g; leucine 8.5 g; lysine malate 7.86 g; L-methionine 0.5 g; phenylalanine 0.25 g; threonine 1.2 g; tryptophane 0.1 g; valine 6.4 g; L-arginine 4.9 g; histidine 0.6 g; acetylcysteine 0.2 g; alanine 2.1 g; glycine 0.7 g; L-glutamic acid 1 g; ornithine L-aspartate 8.03 g; proline 1.2 g; serine 2.75 g); sorbitol 25 g; xylitol 25 g; sodium 30 mmoles; potassium 18 mmoles; magnesium 5 mmoles; chloride 28 mmoles; malate 28 mmoles; phosphate 15 mmoles. For the treatment with the combination the Aminofusin-Hepar infusion solution was admixed with human hair hydrolyzate and sodium thiocyanate (300 mg SCN⁻ per 1 liter of infusion solution). In parallel tests, the same doses of sodium thiocyanate alone and of the mixture comprising only the human hair hydrolyzate and the infusion solution were tested. Each of the preparations was applied as a hair pack (cf. Table 4) for 20 minutes, followed by a hairwash 2 hours later.

Due to an interaction between the substances combined above there is a distinct enhancement of the hair growth-stimulating thiocyanate effect, which also pertains to the shine and shapability of the hair. Moreover, there is possibly provided an improved bioavailability of thiocyanate by the addition of short-chain and higher molecular weight peptides and/or proteins.

Example 11

In accordance with Example 3, the combination of 0.5% of lactic acid and sodium thiocyanate (200 mg of SCN⁻ per 1 liter of drinking water) was tested with guinea pigs. As a control both 0.5% of lactic acid and sodium thiocyanate were tested alone at the same dose as in the combination.

Lactic acid alone did not exhibit any determinable significant influence onto the growth of the hair. The effect caused by the combination of thiocyanate with lactic acid was significantly superior to that caused by thiocyanate alone, as was evident from the shift in favor of the anagenic phase.

Example 12

In test persons suffering from *Alopecia totalis* there were compared the effects caused by a UV irradiation method and by an application of sodium thiocyanate with the effect caused by both measures in combination, each group comprising 5 test persons. The UV irradiation of the whole body was carried out in the form of the PUVA therapy (combination of 8-methoxy-psoralen with UV-A radiation) twice a week, beginning with an exposition period of 2 minutes. The irradiation was effected using Narva radiation (UVS 40-2, cumulative dose 51 J/cm$^2$). Sodium thiocyanate was applied as a hair pack according to Example 5. Upon the combined application of both measures, first the hair pack with sodium thiocyanate was applied, and 30 minutes thereafter the irradiation was carried out as described above.

Upon the PUVA therapy alone, 2 among 5 of the test persons exhibited a beginning growth of the hair after a 4 weeks' period of treatment; these test persons lost their hair again three months after the discontinuation of the therapy. Upon the application of thiocyanate alone, the hair of 4 among 5 test persons began to grow, whereupon the maximum of hair growth was reached after a treatment period of ¼ of a year. In the same manner the hair of 4 among 5 test persons began to grow after the application of sodium thiocyanate and PUVA therapy in combination; however, a higher degree was attained in the latter case (the difference between the two groups, relative to the area and hair denseness, according to Table 1 was 1.2 points).

In addition, investigations with guinea pigs were carried out in order to elucidate possible mechanisms of action. In guinea pigs, UV radiation (UV-A: 92%, UV-B: 8%, radiation intensity in the irradiated area 2 mW/cm$^2$) induced a decrease in the SCN⁻ content of the skin of guinea pigs. The following Table 6 shows the thiocyanate content (mg/kg FM) in guinea pig skin (skin sample of an area of 3 cm×3 cm) on day 29 of the test.

TABLE 6

| Control animals | | | UV irradiation[1] | Probability of error (%) for the control |
|---|---|---|---|---|
| n | X | s | | |
| 10 | 1.0 | 0.37 | 0.7 0.3 | 5 |

[1]UV irradiation for 28 days (including weekend breaks) 5 minutes daily, 15 minutes on day 28.

Moreover, the UV irradiation counteracted a stress-related SCN⁻ increase as determinable in the serum in a control group, which is evident from Table 7 showing the thiocyanate serum levels in mg/ml.

TABLE 7

| Day of the test | UV irradiation[1] | | | Control animals | | | Probability of of error (%) for the control |
|---|---|---|---|---|---|---|---|
| | n | X | s | n | X | s | |
| 1st | 18 | 3.2 | 0.71 | 19 | 3.2 | 0.91 | — |
| 8th | 18 | 5.1 | 0.83 | 19 | 4.4 | 1.13 | 5 |
| 15th | 18 | 4.8 | 0.88 | 19 | 4.3 | 1.28 | — |
| 21st | 18 | 4.1 | 0.76 | 19 | 4.0 | 1.07 | — |

[1]Begin of the irradiation on the 2nd day of the test with 15 minutes, prolongation by 5 minutes per day; after each weekend break, 10 minutes were subtracted from the amount of the latest reached irradiation period and then the period of irradiation was analogously prolongated by 5 minutes per day.

We claim:

1. A preparation for hair, comprising A) at least one of alkali metal, alkaline earth metal, and ammonium salts of thiocyanic acid and B) at least one of estrogens, sulfur, sulfide ions, vasodilators, skin-active vitamins, inorganic selenium compounds, amino acids, and carboxylic acids physiologically occurring in the skin or mixtures thereof, wherein thiocyanate ions are present in a concentration of from 0.001 to 1% by weight based on the total weight of the preparation.

2. A preparation for hair, comprising A) at least one of alkali metal, alkaline earth metal, and ammonium salts of thiocyanic acid and B) at least one protein hydrolyzate, wherein thiocyanate ions are present in a concentration of from 0.001 to 1% by weight based on the total weight of the preparation.

3. The preparation according to claim 1, wherein the alkali metal salt of thiocyanic acid is selected from the group consisting of sodium and potassium salts.

4. The preparation according to claim 1, wherein the estrogen is an estradiol that is present in a concentration of from 0.02 to 6 mg/l.

5. The preparation according to claim 4, wherein the estradiol is estradiol benzoate.

6. The preparation according to claim 1, wherein sulfur is present in the form of colloidal sulfur.

7. The preparation according to claim 6, wherein colloidal sulfur is present in the preparation in a concentration of from 0.001 to 20 mg/l.

8. The preparation according to claim 1, wherein sulfide ions are present in the preparation in a concentration of from 0.001 to 0.1 mg/l.

9. The preparation according to claim 1, wherein a vasodilator is present in the preparation in a concentration of from 1 to 50 mg/l.

10. The preparation according to claim 9, wherein the vasodilator is propyl nicotinate.

11. The preparation according to claim 1, wherein a skin-active vitamin is present in the preparation in a concentration of from 1 to 50 mg/l.

12. The preparation according to claim 11, wherein the skin-active vitamin is Dexpanthenol.

13. The preparation according to claim 1 wherein at least one alkali metal selenocyanate is present in the preparation in a concentration of from 0.01 to 5 mg/l.

14. The preparation according to claim 13, wherein the alkali metal selenocyanate is potassium selenocyanate.

15. The preparation according to claim 1, containing at least one amino acid is present in the preparation in a concentration of from 1 to 150 g/l.

16. The preparation according to claim 1, wherein mixtures of at least one of amino acids and protein hydrolyzates are present in the preparation in a total concentration of from 1 to 150 g/l.

17. The preparation according to claim 1, wherein a carboxylic acid physiologically occurring in the skin is present in the preparation in a concentration of from 1 to 100 g/l.

18. A preparation for hair, comprising A) at least one of alkali metal, alkaline earth metal, and ammonium salts of thiocyanic acid, B) at least one of estrogens, sulfur, sulfide ions, vasodilators, skin-active vitamins, inorganic selenium compounds, amino acids, and carboxylic acids physiologically occurring in the skin or mixtures thereof, and C) auxiliary and carrier materials selected from the group consisting of ethanol, glycerol, alkali metal alkanesulfonates, polyethyleneglycols, wool wax alcohols, triglycerides, and *Alcoholes emulsivicantes*, wherein thiocyanate ions are present in a concentration of from 0.001 to 1% by weight based on the total weight of the preparation.

19. The preparation according to claim 1, wherein the A) component and the B) component are present separately from each other.

20. A method comprising:
    a step of applying of a preparation comprising A) at least one of alkali metal, alkaline earth metal, and ammonium salts of thiocyanic acid, and B) at least one of estrogens, sulfur, sulfide ions, vasodilators, skin-active vitamins, inorganic selenium compounds, amino acids, protein hydrolyzates, and carboxylic acids physiologically occurring in the skin, or mixtures thereof, wherein thiocyanate ions are present in a concentration of from 0.001 to 1% by weight based on the total weight of the preparation.

21. The method according to claim 20, wherein said applying step is a step of topical application.

22. The method according to claim 21, wherein the method is applied in response to alopecia.

23. A method according to claim 20 wherein the preparation is used in the form of a solution, emulsion, dispersion, gel or ointment.

24. The method according to claim 20, further comprising using the preparation in combination with a physiologically active ultra-violet radiation.

25. The method according to claim 20, wherein the topical application of active components A) and B) is effected simultaneously.

26. The method according to claim 20, wherein the topical application of active components A) and B) is effected sequentially.

27. A method according to claim 20, wherein a topical application is accomplished by inclusion of the preparation in medical bath waters, shower lotions, hair tonics, hair shampoos, hair care agents and cosmetics.

28. A method comprising:
    a step of applying to a subject a composition comprising A) at least one of alkali metal, alkaline earth metal, and ammonium salts of thiocyanic acid and B) at least one protein hydrolyzate, wherein thiocyanate ions are present in a concentration of from 0.001 to 1% by weight based on the total weight of the composition.

29. A preparation for hair, comprising A) at least one of alkali metal, alkaline earth metal, and ammonium salts of thiocyanic acid, B) at least one protein hydrolyzate, and C) auxiliary and carrier materials selected from the group consisting of ethanol, glycerol, alkali metal alkanesulfonates, polyethyleneglycols, wool wax alcohols, triglycerides, and *Alcoholes emulsivicantes*, wherein thiocyanate ions are present in a concentration of from 0.001 to 1% by weight based on the total weight of the preparation.

30. A method comprising:
    a step of applying a preparation comprising A) at least one of alkali metal, alkaline earth metal, and ammonium salts of thiocyanic acid, and B) at least one of estrogens, sulfur, sulfide ions, vasodilators, skin-active vitamins, inorganic selenium compounds, amino acids, protein hydrolyzates, and carboxylic acids physiologically occurring in the skin, or mixtures thereof, and C) auxiliary and carrier materials selected from the group consisting of ethanol, glycerol, alkali metal alkanesulfonates, polyethyleneglycols, wool wax alcohols, triglycerides, and *Alcoholes emulsivicantes*, wherein thiocyanate ions are present in a concentration of from 0.001 to 1% by weight based on the total weight of the preparation.

* * * * *